United States Patent

Van Dijk et al.

[11] Patent Number: 5,773,526
[45] Date of Patent: Jun. 30, 1998

[54] METHOD AND DEVICE FOR ANAEROBIC FERMENTATION OF SOLID ORGANIC WASTE SUBSTANCES

[75] Inventors: Meine Van Dijk, Harich; Jelle Faber, Elahuizen, both of Netherlands

[73] Assignee: Paques Solid Waste Systems B.V., Balk, Netherlands

[21] Appl. No.: 809,041

[22] PCT Filed: Aug. 25, 1995

[86] PCT No.: PCT/NL95/00284

§ 371 Date: Apr. 3, 1997

§ 102(e) Date: Apr. 3, 1997

[87] PCT Pub. No.: WO96/07726

PCT Pub. Date: Mar. 14, 1996

[30] Foreign Application Priority Data

Sep. 7, 1994 [NL] Netherlands ............... 9401454

[51] Int. Cl.[6] .................. C12M 1/113; C02F 11/04
[52] U.S. Cl. ............ 210/603; 210/608; 210/194; 210/218; 210/539
[58] Field of Search .................. 210/603, 608, 210/609, 613, 194, 218, 525, 539

[56] References Cited

U.S. PATENT DOCUMENTS 3,981,803  9/1976  Coulthard ............... 210/218
4,334,997  6/1982  Peterson ............... 210/603
4,372,856  2/1983  Morrison ............... 210/603
4,735,724  4/1988  Chynoweth et al. ....... 210/603
4,826,600  5/1989  Ely et al. ............. 210/603
5,228,995  7/1993  Stover ................. 210/194
5,616,241  4/1997  Khudenko .............. 210/218

FOREIGN PATENT DOCUMENTS 888670    8/1981  Belgium .
0 048 675  3/1982  European Pat. Off. .
2 204 056  11/1988  United Kingdom .

*Primary Examiner*—Thomas G. Wyse
*Attorney, Agent, or Firm*—Young & Thompson

[57] ABSTRACT

For the anaerobic fermentation of solid organic waste substances, solid waste is mixed with liquid material, particularly anaerobic slurry, and the temperature of the mixture is brought to a value between 25° and 70° C., preferably between 30° and 40° C. (mesophilic) and between 55° and 65° C. (thermophilic). By means of spontaneous rising of lightweight material and by means of flotation, a layer (10) of solid material floating on a methane-generating zone is formed from said mixture in a reactor. Said floating layer moves from a supply end (7) or a mixing section (2) to a discharge end (14) of the reactor, hydrolysis and acidification of solidorganic material taking place in the floating layer. The fermented floating layer is discharged via the discharge (14) end independent of the residence time of fluid and slurry in the methane-generating zone under the floating layer.

9 Claims, 1 Drawing Sheet

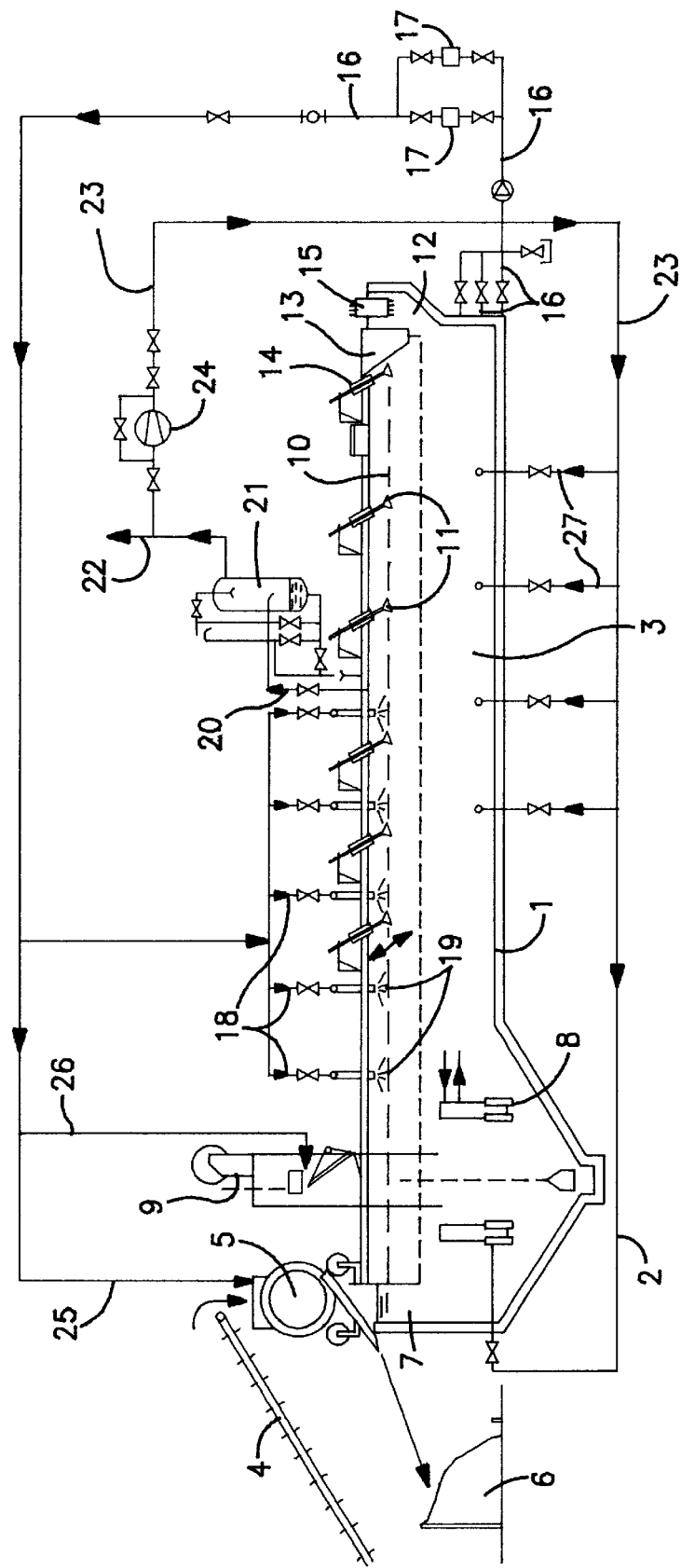

METHOD AND DEVICE FOR ANAEROBIC FERMENTATION OF SOLID ORGANIC WASTE SUBSTANCES

In the first instance, the invention relates to a method for the anaerobic fermentation of solid organic substances in a reactor tank in which there is a mixture of the solid organic substances and an anaerobic fluid, in which a layer of material floating on a methanegenerating fluid is moved from a supply end to a discharge end of said reactor tank and a methane-forming reaction is induced in the methane-generating fluid under the floating layer, and in which fluid is sprayed in and/or on the floating layer.

Such a method is described in U.S. Pat. No. 4334997.

Solid waste substances may consist, inter alia, of vegetable, fruit and garden waste, household waste and organic industrial waste.

Purification of sewage and the processing of manure has, for decades, employed fermentation processes. Fermentation leads to the production of biogas and to stabilization of waste or slurry. Increasingly, however, fermentation processes are also being used to process waste from the agro-industry and household waste (such as vegetable, fruit and garden waste).

When use is made of a completely mixed reactor or a plug-flow reactor, the residence times of the waste to be fermented and of the biomass (methane-generating sludge) are identical to each other. However, the growth rate of methane-generating bacteria is relatively low, which results in the residence time of the biomass and thus of the material to be fermented having to be relatively long (20 to 30 days). This results in relatively long reactor tanks. Although systems are known in which a separation is brought about between the residence times of fermenting material and methane-generating biomass, they usually make use of a plurality of reactors with complicated separation systems between them. This also leads to high production and operating costs.

In the method according to the abovementioned US patent specification, the floating layer is moved and discharged independent of the methane-generating fluid zone. In other words, the residence times of the floating layer and the methane-generating slurry do not have to be identical to each other. The fluid sprayed on the floating layer consists of deoxygenated water which fulfils only a transport function for the floating layer. The fluid will have to be vigorously squirted onto and in the floating layer, which will also have a mixing effect and, as a result of this, solid portions of the floating layer are squirted into the methane-generating fluid, to the detriment of the thickness of the floating layer. In each case, no attempt is made to ferment the components of the floating layer. The floating layer is regarded only as an inconvenience and is therefore kept as thin as possible. The floating layer is discharged from the reactor tank as quickly as possible.

The object of the invention is to generate a controlled fermentation reaction in the floating layer.

To this end, the method mentioned in the preamble is characterized in that the fluid sprayed in and/or on the floating layer is extracted from the methane-generating zone under the floating layer in order to induce fermentation in the floating layer and also, by means of percolation, to remove acid fermentation products from the floating layer and to drive them to the methane-generating zone under the floating layer, and in that the floating layer is moved in such a controlled manner that the said fermentation reaction can take place in the floating layer.

Solid waste and anaerobic slurry could be mixed outside the reactor, but it is preferable for this mixing to be carried out in a mixing section of the actual reactor.

During mixing, heavy material which has sunk has to be removed periodically.

The anaerobic slurry will have to be brought to the desired temperature in order to achieve adequate fermentation performance levels. In the case of the mesophilic bacteria, this means that the temperature has to be brought to between approximately 30° and approximately 40° C., whilst in the case of thermophilic bacteria, a temperature of between approximately 55 and approximately 65° C. is favourable.

According to the invention, by means of spontaneous floatation of the light solid material and sinking of the biomass, a separation is brought about between said two materials, and both materials are fermented adequately independently and in their own time. It is essential that fluid from the methane-generating zone is sprayed in and/or on the floating layer, by means of which fermentation in the floating layer is achieved.

The biogas formed in the methane-generating zone flows upwards and bubbles through the floating layer, as a result of which, on the one hand, the floatation is enhanced and, on the other hand, mixing and breaking-open of the floating layer take place. Mixing can be intensified if the fluid withdrawn from the methane-generating zone is also used to improve the intake of solid material and mixing.

The 1- to 2-meter-thick floating layer will be broken up to a certain degree and the contents of the reactor will be better mixed if the biogas formed is at least partially recirculated by being injected, at different locations, into the lower portion of the reactor.

The residence time of the fermenting material in the floating layer in the reactor is approximately 5 days. During this time, the floating layer is moved towards the discharge end of the reactor using mechanical means.

At the discharge end of the reactor, the floating layer is pushed under a baffle forming part of a water seal or is removed via another mechanism. The baffle can be adjusted in order to regulate the thickness of the floating layer.

The invention also relates to a reactor for implementing the above method, comprising a reactor tank with a supply end for a mixture of solid waste and anaerobic fluid and a discharge end for a layer floating on the methane-generating fluid, means for moving the floating layer from the supply end to the discharge end, and means for spraying fluid in and/or the floating layer and means for discharging the floating layer out of the reactor, via a water seal, at the discharge end independent of the fluid and slurry located under the floating layer.

Such a reactor is also known from said U.S. Pat. No. 4334997.

In order to be able to implement the method according to the invention, the means for spraying fluid in and/or on the floating layer are connected to lines which can extract fluid from the methanegenerating zone under the floating layer.

In this case, means may be present for discharging the biogas formed in the reactor which are installed at different locations at the bottom of the reactor.

The means for moving the floating layer may consist of a hydraulically movable blade which can hinge in the forward direction of the floating layer, and can execute a downward translational movement in the floating layer during said hinging movement, and. when it has reached an approximately vertical position can move upwards to a position outside the floating layer and, finally, can hinge back to the starting position. A blade could also be moved mechanically to follow a parallelogram-shaped path: in sequence, obliquely forwards, in the direction of the discharge end of the reactor, obliquely back upwards and, finally, in the direction of the supply end of the reactor.

The invention will now be described in greater detail on the basis of the figure which gives a diagrammatic illustration of the reactor according to the invention.

The figure shows a reactor tank 1 which is closed at the top, consisting of a mixing part 2 and a fermentation part 3.

A supply conveyor 4 for solid organic waste, such as vegetable, fruit and garden waste, opens out, via its discharge end, above a rotating drum sieve 5 which separates the very coarse material, such as branches, car tyres and concrete blocks from the waste for fermentation formed by the material which passes through the sieve. The very coarse waste falls onto a storage area 6 and the material passing through the sieve falls via an inlet 7, designed like a water seal, into the mixing part 2. in said part, stone, glass, ceramic material, metal and coarse sand sink to the bottom and the newly arrived components to be fermented and methane-generating biomass in the reactor are mixed. Then, in the mixing part, the mixture is heated to a temperature of between 25° and 70° C., preferably between 30° and 40° C. (mesophilic) or between 55 and 65° C. (thermophilic) by means of heating/mixing units 8. The latter ones consist of double-walled vertical nozzles in whose cavity hot water flows. From time to time, the material which has sunk and is lying on the bottom of the mixing part is removed by means of a grab-crane 9.

In the fermentation portion 3, the actual biological conversions take place, as a result of which, owing to the rising up of the fibrous material and flotation, caused by rising bubbles of biogas, a floating layer 10 is formed with a thickness of 1 to 2 meters. Said layer is pushed by means of hydraulically driven blades 11 in the direction of the discharge end 14 of the reactor, which discharge end is designed as a water seal. Before said discharge end there is a baffle 13 and a plunger 12 for pushing the fermented material of the floating layer 10 under the baffle 13 through towards the water seal 14, which allows the material to fall onto a discharge area. The blades 11 can hinge in the forward direction of the floating layer and, simultaneously, describe a downward translational movement. When said blades have reached a vertical position, they move upwards and hinge towards the starting position.

During the approximately 5-day-long transportation of the material in the floating layer, from the intake 7 to the outlet 12, organic material is hydrolysed and acidified, while methane is also formed in the floating layer. At a pH of between 6 and 7, solid substances, such as starch and protein, are biologically converted into dissolved substances such as sugar, acetic acid and amino acids. The acidification products must not accumulate because, in the event of a highly acidified floating layer, the biological decomposition process will be halted. Discharge of acidification products from the floating layer towards the methane-generating zone underneath takes place by percolation through the floating layer of buffer fluid which is drawn off by means of lines 16 and sieves 17 from the methane-generating zone and is returned via lines 18 and spraying heads 19 in and/or on the floating layer. The drawn-off fluid also contributes to fermentation in the floating layer.

The dissolved acidification products are converted into biogas in the methane-generating biomass under the floating layer 10. Said biogas flows upwards and leaves the reactor via the line 2C after it has bubbled through the floating layer, which gives rise to extra mixing and opening-up of the floating layer. As a result of this, there will be no formation of a crust, blind spots or dead spaces.

The biogas flows via the line 20 to a tank 21 in which foam is separated off. From there, the gas flows via a discharge line 22 towards, for example, a generator. A branch line 23 of the line 22 carries a portion of the biogas, after the latter has passed through a compressor 24, to a number of lines 27 opening out in the lowermost portion of the reactor. Said extra biogas intensifies the mixing in the methane-generating zone and causes greater opening-up of the floating layer.

The fluid drawn off from the methane-generating zone via the line 16 can, in addition to being used for said percolation through the floating layer, be used for improving the supply and mixing of the fermented material (see line 25) and for spraying the material which has been collected by the crane 9 (see line 26).

The degree of acidity in the floating layer will be between 6 and 7 and that in the methane-generating slurry between 7 and 8.

The most important advantage of the reactor described and the method described is that the residence times of the floating layer and methane-generating zone may be different without complicated apparatus. The residence time of the material in the floating layer is approximately 5 days and that in the methane-generating zone, depending on the dry-matter content (which is usually less than 7%) 20 days, for example. Furthermore, the fermentation in the floating layer itself is enhanced.

The fermented material discharged can, for example, be processed into compost.

The slurry discharged from the methane-generating zone can be separated out in a centrifuge, resulting in water on the one hand and a solid substance and methane bacteria on the other.

Various modifications and additions are possible within the scope of the invention.

We claim:

1. Method for the anaerobic fermentation of solid organic substances in a reactor tank (1) in which there is a mixture of the solid organic substances and an anaerobic fluid, in which a layer of material (10) floating on an anaerobic methane-generating fluid is moved from a supply end (7) to a discharge end (14) of said reactor tank and a methane-forming reaction is induced in the anaerobic methane-generating fluid under the floating layer (10), and in which fluid is sprayed in and/or on the floating layer (10), characterized in that the fluid sprayed in and/or on the floating layer is extracted from the anaerobic methane-generating zone under the floating layer (10) in order to induce fermentation in the floating layer and also, by means of percolation, to remove acid fermentation products from the floating layer and to drive them to the anaerobic methane-generating zone under the floating layer, and in that the floating layer (10) is moved in such a controlled manner that the said fermentation reaction can take place in the floating layer.

2. Method according to claim 1, characterized in that mixing of the solid waste and anaerobic methane-generating fluid takes place in a mixing section (2) of the reactor.

3. Method according to claim 1, characterized in that, during mixing, heavy material which has sunk is periodically removed.

4. Method according to claim 1, characterized in that fluid from the anaerobic methane-generating zone is also used to improve the intake of solid material and mixing.

5. Method according claim 1, characterized in that said methane is at least partially recirculated by being injected, at different locations, into the lower portion of the reactor (1).

6. Method according to claim 1, characterized in that the floating layer (10) is moved to the discharge end (14) of the reactor using mechanical means (11).

7. Reactor for the anaerobic fermentation of solid organic substances, comprising a reactor tank (1) with a supply end (7) for a mixture of solid waste and anaerobic methane generating fluid and a discharge end (14) for a layer (10) floating on the anaerobic methane-generating fluid, means (11) for moving the floating layer from the supply end (7) to the discharge end (14), and means (19) for spraying fluid in and/or on the floating layer and means (12, 13) for discharging the floating layer out of the reactor, via a water seal (14), at the discharge end independent of the fluid and slurry located under the floating layer, characterized in that the means (19) for spraying fluid in and/or on the floating layer are connected to leads (18) which can withdraw the fluid from the anaerobic methane-generating zone under the floating layer (10).

8. Reactor according to claim 7, characterized by means (27) for discharging the methane formed in the reactor and to supply said methane at different locations in the bottom of the reactor.

9. Reactor according to claim 7, characterized by mechanical means (11) for moving a floating layer (10) formed in the reactor (1) in a controlled manner to the discharge end (14) of the reactor.

* * * * *